United States Patent [19]
Mewshaw et al.

[11] Patent Number: 6,162,803
[45] Date of Patent: Dec. 19, 2000

[54] INDOL-3-YL-CYCLOHEXYL AMINE DERIVATIVES FOR THE TREATMENT OF DEPRESSION

[75] Inventors: Richard E. Mewshaw, Princeton; Ping Zhou, Plainsboro, both of N.J.

[73] Assignee: American Home Products Corp., Madison, N.J.

[21] Appl. No.: 09/287,676

[22] Filed: Apr. 7, 1999

Related U.S. Application Data

[60] Provisional application No. 60/104,595, Apr. 8, 1998.

[51] Int. Cl.[7] .................. A61K 31/536; A61K 31/4985; C07D 413/08; C07D 241/38; C07D 215/12
[52] U.S. Cl. .............. 514/230.5; 514/249; 514/314; 514/415; 544/143; 544/144; 544/353; 544/354; 544/356; 546/152; 546/153; 548/469; 548/504
[58] Field of Search ................. 514/230.5, 249, 514/314, 415; 544/143, 144, 353, 354, 356; 546/152, 153; 548/469, 504

[56] References Cited

U.S. PATENT DOCUMENTS

| | | | |
|---|---|---|---|
| 3,058,980 | 10/1962 | Berg et al. | 260/244 |
| 4,612,312 | 9/1986 | Hibert et al. | 514/225 |
| 5,126,363 | 6/1992 | Jeppesen et al. | 514/410 |

FOREIGN PATENT DOCUMENTS

WO8907596   8/1989   WIPO.

OTHER PUBLICATIONS

Artigas et al., Acceleration of the Effect of Selected Antidepressant Drugs in Major Depression by 5–HT$_{1A}$ Autogonists. *Trends Neurosci.*, 19:378–383 (1996).

*Primary Examiner*—Mukund J. Shah
*Assistant Examiner*—Ben Schroeder
*Attorney, Agent, or Firm*—Michael R. Nagy

[57] ABSTRACT

Compounds effective in treating disorders of the serotonin-affected neurological symptoms are provided, such compounds having the following formula:

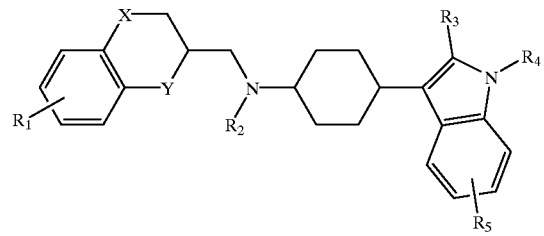

wherein:

$R_1$ and $R_5$ are each, independently, hydrogen, halogen, lower alkoxy, lower alkyl, cyano, or trifluoromethyl;

$R_2$ and $R_4$ are each, independently, hydrogen, lower alkyl, phenyl, or substituted phenyl;

$R_3$ is hydrogen or lower alkyl; and

X and Y are each, independently, O, $NR_6$, or $CH_2$, wherein $R_6$ is hydrogen, lower alkyl, phenyl, or substituted phenyl; or pharmaceutically acceptable salts thereof.

8 Claims, No Drawings

INDOL-3-YL-CYCLOHEXYL AMINE DERIVATIVES FOR THE TREATMENT OF DEPRESSION

CROSS REFERENCE TO RELATED APPLICATIONS

This application claims the benefit of U.S. Provisional Application No. 60/104,595, which was converted from U.S. patent application Ser. No. 09/057,244, filed Apr. 8, 1998, pursuant to a petition filed under 37 C.F.R. 1.53(c)(2)(i) filed Jul. 30, 1998.

FIELD OF INVENTION

This invention relates to compounds useful for the treatment of diseases affected by disorders of the serotonin-affected neurological systems, such as depression and anxiety. More specifically, this invention relates to various indol-3-yl-cyclohexylamine derivatives useful for the treatment of such diseases.

BACKGROUND OF INVENTION

Pharmaceutical compounds which enhance the transmission of serotonin (5-HT) are useful for the treatment of many psychiatric disorders, including depression and anxiety. The first generation of non-selective serotonin-affecting drugs operated through a variety of physiological functions which cause them to possess numerous undesired side effects, such as blurred vision, dry mouth, and sedation. The more recently introduced compounds, the selective serotonin reuptake inhibitors (SSRIs), act predominately by inhibiting 5-HT, which is released at the synapses, from being actively removed from the synaptic cleft via a presynaptic serotonin transport carrier. Since SSRIs require several weeks before they exert their full therapeutic effect, this 5-HT blockade mechanism cannot fully account for their therapeutic activity. It is speculated that this two week induction which occurs before a full antidepressant effect is observed, is due to the involvement of the 5-HT1A autoreceptors which suppress the firing activity of the 5-HT neurons, causing a dampening of the therapeutic effect. Studies suggest that after several weeks of SSRI administration, a desensitization of the 5-HT autoreceptors occurs allowing a full antidepressant effect in most patients. Hence, it is believed that overriding the negative feedback with the 5-HT1A antagonists would increase and accelerate the clinical antidepressant response. Recent studies by Artigas et al., *Trends Neurosci.*, 19:378–383 (1996) suggest a combination of 5-HT1A activity and inhibition of 5-HT uptake within a single molecular entity can achieve a more robust and fast-acting antidepressant effect.

U.S. Pat. No. 3,058,980 discloses the preparation of compounds having the following formula which are claimed to exhibit analgesic activity.

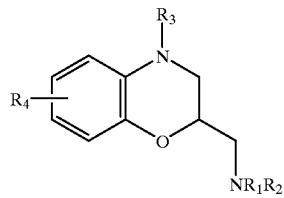

PCT Patent No. WO 89-07596A discloses the preparation of compounds of the following formula which are active in a variety of central nervous system disorders, including depression and schizophrenia.

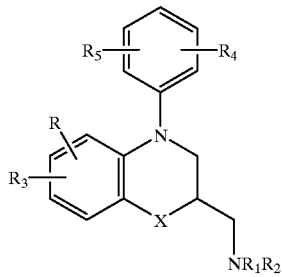

Lastly, U.S. Pat. No. 4,612,312 discloses compounds of the following formula as being potentially useful as anxiolytic and antihypertensive agents.

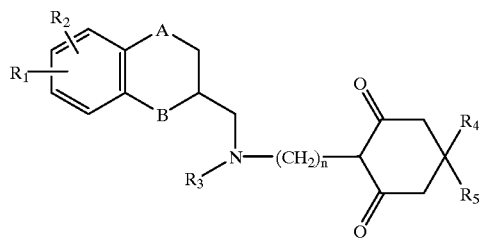

SUMMARY OF THE INVENTION

The present invention is directed to novel molecules which have the ability to act concomitantly at the 5-HT1A autoreceptors and with the 5-HT transporter. Such compounds are, therefore, potentially useful for the treatment of depression and other serotonin disorders.

The compounds of the present invention are indol-3-yl-cyclohexyl amine derivatives represented by Formula I:

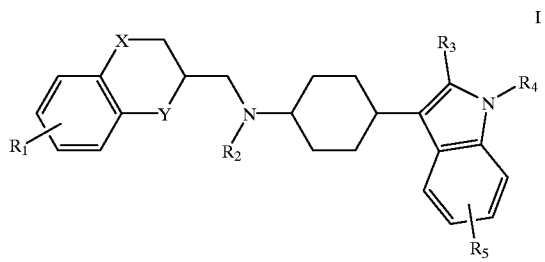

wherein:
  $R_1$ and $R_5$ are each, independently, hydrogen, halogen, lower alkoxy, lower alkyl, cyano, or trifluoromethyl;
  $R_2$ and $R_4$ are each, independently, hydrogen, lower alkyl, phenyl, or substituted phenyl;
  $R_3$ is hydrogen or lower alkyl; and
  X and Y are each, independently, O, $NR_6$, or $CH_2$, wherein
    $R_6$ is hydrogen, lower alkyl, phenyl, or substituted phenyl; or pharmaceutically acceptable salts thereof.

DETAILED DESCRIPTION OF THE INVENTION

Preferably, the compounds of the present invention are those represented by Formula I, wherein:
  $R_1$ and $R_5$ are each, independently, hydrogen, or halogen;
  $R_2$ and $R_4$ are each hydrogen;

$R_3$ is hydrogen; and

X and Y are each, independently, O or $NR_6$, wherein $R_6$ is hydrogen; or pharmaceutically acceptable salts thereof More specifically, the compounds of the present invention are selected from the following:

(3,4-Dihydro-benzo[1,4]oxazine-2-ylmethyl)-[cis-4-(5-fluoro-1H-indol-3-yl)-cyclohexyl]-arnine;

(3,4-Dihydro-benzo[1,4]oxazine-2-ylmethyl)-[trans-4-(5-fluoro-1H-indol-3-yl)-cyclohexyl]-amine;

(3,4-Dihydro-benzo[1,4]oxazine-3-ylmethyl)-[cis-4-(5-fluoro-1H-indol-3-yl)-cyclohexyl]-amine; and (3,4-Dihydro-benzo[1,4]oxazine-3-ylmethyl)-[trans-4-(5-fluoro-1H-indol-3-yl)-cyclohexyl]-amine.

As used herein, the terms "lower alkyl" and "lower alkoxy" are meant to include straight and branched carbon chains containing 1–6 carbon atoms. The term "halogen" is meant to include fluorine, chlorine, bromine, and iodine.

The compounds of Formula I also may be used in the form of a pharmaceutically acceptable acid addition salt having the utility of the free base. Such salts, prepared by methods well known to the art are formed with both inorganic or organic acids, for example: fumaric, maleic, benzoic, ascorbic, pamoic, succinic, bismethylenesalicylic, methanesulfonic, ethanedisulfonic, acetic, oxalic, propionic, tartaric, salicyclic, citric, gluconic, lactic, malic, mandelic, cinnamic, citraconic, aspartic, stearic, palmitic, itaconic, glycolic, p-aminobenzoic, glutamic, benzene-sulfonic, hydrochloric hydrobromic, sulfuric, cyclohexylsulfamic, phosphoric and nitric acids.

The compounds of the present invention may be prepared by any suitable method known to those skilled in the art. However, the present compounds may be prepared according to any one of Schemes 1–3 set forth below. In the Schemes, the intermediate compounds exemplified hereinafter are identified in parenthesis. The compound produced in each of the Schemes is identified by reference to the appropriate Example.

The compounds of Formula I are generally prepared by the overall sequence indicated in Schemes 1–3 as follows. In the Schemes, the intermediate compounds exemplified hereinafter are identified in parenthesis. The compound produced in each of Schemes 1 to 3 is identified by reference to the appropriate Example.

Scheme 1

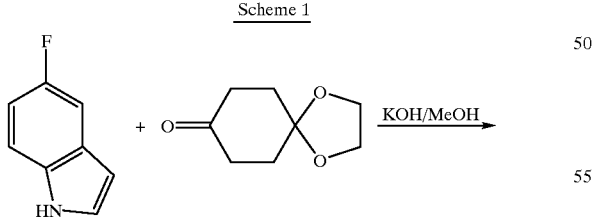

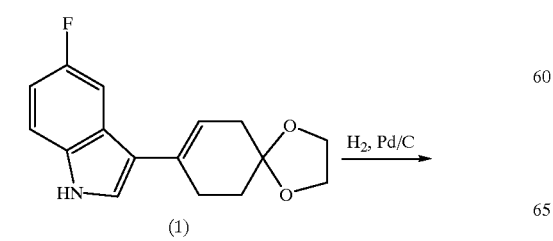

(1)

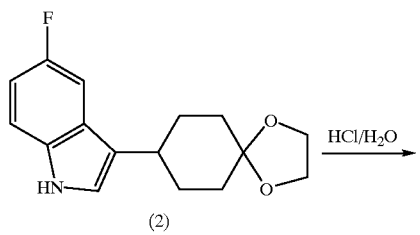

(2)

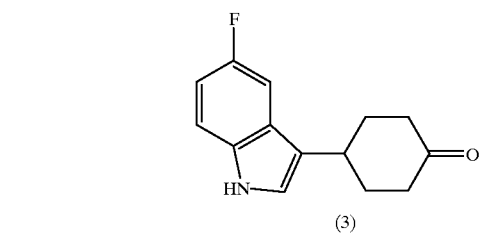

(3)

Scheme 2

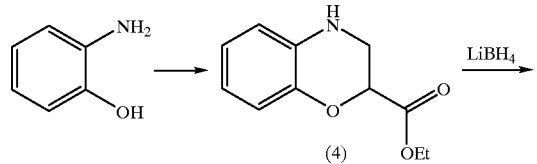

(4)

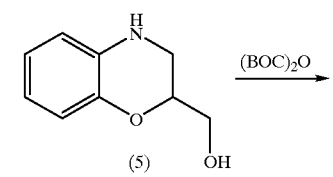

(5)

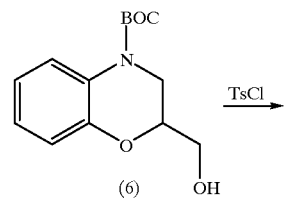

(6)

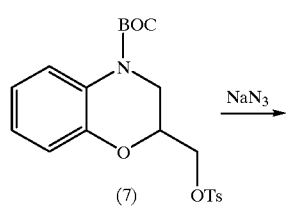

(7)

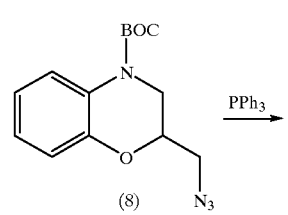

(8)

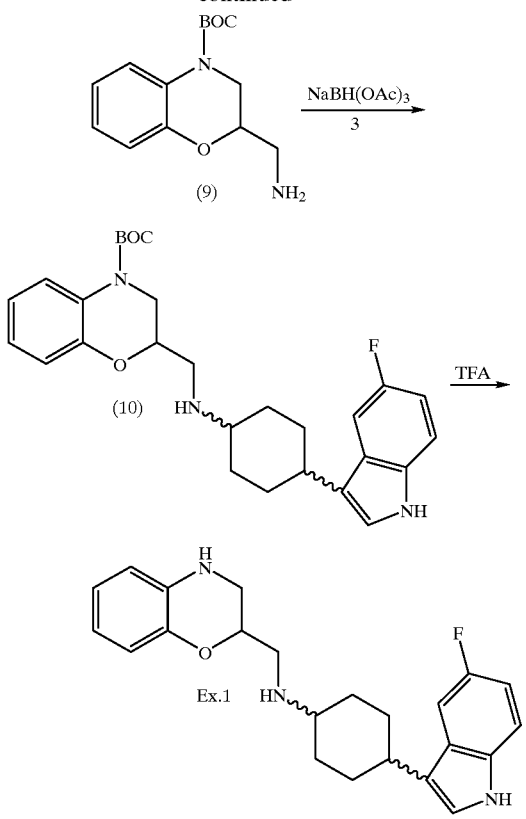

Scheme 3

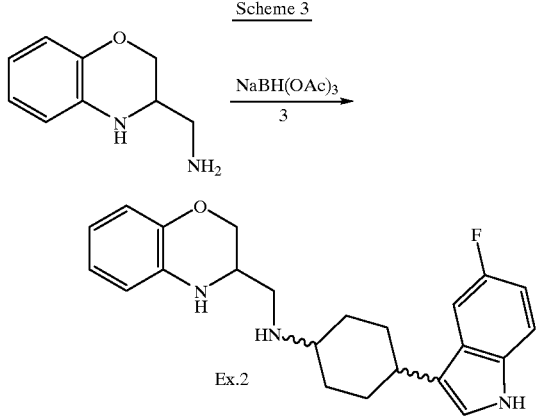

The present invention will now be illustrated by reference to the following specific non-limiting examples.

INTERMEDIATE 1

4-(5-Fluoro-1H-3-indolyl)-cyclohex-3-en-one ethylene ketal

5-Fluoroindole (5.4 g, 0.04 mol), 1,4-cyclohexanedione monoethylene ketal (12.5 g, 0.08 mol) were placed in 60 ml of 2N potassium hydroxide methanolic solution. The reaction mixture were heated to reflux for 4 hours. The reaction was cooled and the product was isolated by filtration and washed with methanol to give 10.1 g (93%) of product as a white solid: mp 153–155° C.

INTERMEDIATE 2

4-(5-Fluoro-1H-3-indolyl)-cyclohexanone ethylene ketal

A mixture of 4-(5-fluoro-1H-3-indolyl)-cyclohex-3-en-one ethylene ketal (2.7 g, 0.01 mol) and 10% palladium on carbon (1.2 g) in ethanol (200 ml) was hydrogenated for 4 days. The catalyst was filtered off and the filtrate was concentrated. The product was dried under vacuum to afford 2.8 g (100%) of product as a white solid: mp 183–185° C.

INTERMEDIATE 3

4-(5-Fluoro-1H-3-indolyl)-cyclohexanone

A solution of 4-(5-fluoro-1H-3-indolyl)-cyclohexanone ethylene ketal (2.8 g, 0.01 mol) in 200 ml (1:1) tetrahydrofuran-hydrochloric acid (1N) was allowed to stir at room temperature for 16 hours. The mixture was concentrated to half volume. The aqueous was extracted with ethyl acetate. The organic extracts were washed with brine, dried (anhydrous sodium sulfate), and filtered. The crude product was purified by flash chromatography (40% ethyl acetate in hexane) to afford 2.1 g (91%) of product as yellow solid: mp 112–114° C.

INTERMEDIATE 4

2,3-Dihydro-2H-benzo[1,4]oxazine-2-carboxylate ester

To a solution of 2-aminophenol (10.0 g, 0.089 mol) in acetone (100 ml) was added anhydrous potassium carbonate (15.2 g, 0.108 mol) followed by ethyl 2,3-dibromopropionate (23.6 g, 0.092 mol) in four portions at reflux temperature. The reaction mixture was stirred at reflux for 21 hours and cooled. The solid was removed by filtration and the filtrate was concentrated. The residue was dissolved in cold 1N sodium hydroxide and extracted with ethyl ether. The combined organic extracts were washed with brine, dried (anhydrous sodium sulfate), filtered, and concentrated. Chromatography (ethyl acetate/hexane: 1/2) afforded 6.25 g (34.4%) of product as a brown oil:

INTERMEDIATE 5

3,4-Dihydro-2H-benzo[1,4]oxazin-2-yl)-methanol

To a solution of ethyl 2,3-dihydro-2H-benzo[1,4]oxazine-2-carboxylate ester (11.9 g, 19.0 mmol) in anhydrous tetrahydrofuran (60 mL) was added a 2 M solution of lithium borohydride (15 mL) at room temperature. The reaction was allowed to stir for 1 hour and then quenched by the slow addition of methanol. After 2 hours, water was slowly added (100 mL) and the reaction mixture was extracted with ethyl acetate (4×100 mL). The organic layer was separated and dried over anhydrous magnesium sulfate, filtered, and the solvent removed under vacuum. Purification by chromatography (ethyl acetate/hexane/methanol: 3/6/1) afforded 1.96 g (62%) of product as an oil: MS (EI) m/e 165 (M+).

INTERMEDIATE 6

2-Hydroxymethyl-2,3-dihydro-2H-benzo[1,4]oxazine-4-carboxylic acid tert-butyl ester To a solution of 3,4-dihydro-2H-benzo[1,4]oxazin-2-yl)-methanol (10.7 g, 65.0 mmol) in anhydrous tetrahydrofuran (200 mL) was slowly added di-tert-butyl bicarbonate (62 g)

in tetrahydrofuran (40 mL). The reaction was heated to reflux for 4 hours, allowed to cool to room temperature and then poured into water (100 mL) and extracted with ethyl ether (3×100 mL). The organic layer was washed with water (2×50 mL), dried over anhydrous sodium sulfate, filtered, and the solvent removed under vacuum. Chromatography (ethyl acetate/hexane: 1/2) afforded 12.9 g of product as white solid (75%): mp 93.5–94.5° C.; MS (EI) m/e 265 (M+).

Elemental analysis for $C_{14}H_{19}NO_4$; Calc'd: C, 63.38: H, 7.22: N, 5.28. Found: C, 63.53: H, 7.32: N, 5.38.

INTERMEDIATE 7 t-Butyl-2,3-dihydro-2H-benzo[1,4]oxazine-4-carboxylate-2-methyltosylate

To a solution of 2-hydroxymethyl-2,3-dihydro-2H-benzo[1,4]oxazine-4-carboxylic acid tert-butyl ester (80 mg, 0.3 mmol) and p-toluenesulfonyl chloride (86 mg) in anhydrous pyridine (15 mL) was allowed to stir overnight at room temperature. The reaction mixture was quenched with 1N HCl(20 mL) and extracted with methylene chloride (3×20 mL). The organic layer was washed with 1N HCl (2×20 mL) and the organic layer dried over anhydrous sodium sulfate, filtered and the solvent removed under vacuum. Chromatography (ethyl acetate/hexane, 1/2) afforded 120 mg (94%) of product as a thick oil : MS (FAB) m/e 419 (M+Na).

Elemental analysis for $C_{21}H_{25}NO_6S$; Calc'd: C, 60.13: H, 6.01: N, 3.34. Found: C, 60.13: H, 6.11: N, 3.56.

INTERMEDIATE 8 t-Butyl-2,3-dihydro-2H-benzo[1,4]oxazine-4-carboxylate-2-methylazide

A solution of t-butyl-2,3-dihydro-2H-benzo[1,4]oxazine-4-carboxylate-2-methyltosylate (14.2 g, 33.9 mmol) and sodium azide (4.4 g, 67.7 mmol) in anhydrous dimethylformamide (150 nL) was heated to 60° C. for 20 hours. The reaction mixture was poured into water (150 mL) and extracted with methylene chloride (3×150 mL). The combined organic layers were dried over anhydrous sodium sulfate, filtered and the solvent removed under vacuum. Purification by chromatography (hexane) afforded 8.7 g (88%) of product as a white solid: mp 82–83° C.

Elemental analysis for $C_{14}H_{18}N_4O_3$; Calc'd C, 57.92: H, 6.25: N, 19.30. Found: C, 58.07: H, 6.21: N, 19.03.

INTERMEDIATE 9 t-Butyl-2,3-dihydro-2H-benzo[1,4]oxazine-4-carboxylate-2-methylamine

A solution of t-butyl-2,3-dihydro-2H-benzo[1,4]oxazine-4-carboxylate-2-methylazide (6.25 g, 21.6 mmol) and triphenylphosphine (6.4 g) in tetrahydrofuran (150 mL) containing water (4 mL) was allowed to stir at room temperature for 18 hours. The solvent was removed under vacuum. The residue was dissolved in ethyl ether (100 mL). After addition of hexane (50 mL), the precipitated triphenylphosphine oxide was filtered off. The filtrate was concentrated and the residue was purified by chromatography (5% methanol in methylene chloride) affording 7.2 g of product (which contained a small amount of triphenylphosphine oxide).: MS (FAB) m/e 265 (M+H+).

INTERMEDIATE 10

(t-Butyl-3,4-dihydro-benzo[1,4]oxazine-4-carboxylate-2-methyl)-[cis-4-(5-fluoro-1H-indol-3-yl)-cyclohexyl]-amine A solution of 4-(5-fluoro-1H-indol-3-yl)-cyclohexanone (0.74 g,3.2 mmol), t-butyl-2,3-dihydro-2H-benzo[1,4] oxazine-4-carboxylate-2-methylamine (0.80 g, 3.02 mmol), sodium triacetoxyborohydride (1.0 g, 4.5 mmol) and acetic acid (0.18 ml, 3.2 mmol) in 1,2-dichloroethane (14 ml) was allowed to stir at room temperature for 1.5 hours. The reaction was quenched with 1N sodium hydroxide, extracted with methylene chloride. The combined organic extracts were washed with brine, dried (anhydrous sodium sulfate), filtered and concentrated. Chromatography (ethyl acetate/hexane: 3/7 to 5/5) afforded 1.40 g of the title compound product as a cis/trans mixture which was used without further separation.

EXAMPLE 1

(3,4-Dihydro-benzo[1,4]oxazine-2-ylmethyl)-[cis-4-(5-floro-1H-indol-3-yl)-cyclohexyl]-amineand (3,4-Dihydro-benzo[1,4]oxazine-2-ylmethyl)-[trans-4-(5-fluoro-1H-indol-3-yl)-cyclohexyl]-amine To a solution of cis/trans-(t-butyl-3,4-dihydro-benzo[1,4] oxazine-4-carboxylate-2-methyl)-[4-(5-fluoro-1H-indol-3-yl)-cyclohexyl]-amine in methylene chloride (15 ml) was added trifluoroacetic acid (5 ml) at room temperature. After Stirring the reaction mixture at room temperature for 2 hours, the solvent was removed. To the residue was added a small amount of methanol, the solution was adjusted to pH>9 with 2N NaOH. The aqueous was extracted with methylene chloride. The combined organic extracts were washed with brine, dried over anhydrous sodium sulfate, filtered and concentrated. The product was purified by chromatography (EtOAc/MeOH/NH$_4$OH: 99/1/0.5) to afford 0.41 g (35%) of the cis isomer as white solid: mp 65–67° C. The HCl salt of the cis isomer was prepared in ethyl acetate: mp 120° C.(dec)

Elemental analysis for $C_{23}H_{26}FN_3O•2HCl$; Calc'd: C, 61.06; H, 6.24; N, 9.29. Found: C, 61.06; H, 6.40; N, 8.71.

The trans isomer was isolated in 19% yield (0.22 g) as a white solid: 66–68° C. The HCl salt of the trans isomer was prepared in ethyl acetate: mp 155° C. (dec).

Elemental analysis for $C_{23}H_{26}FN_3O•HCl•0.75H_2O•0.33EtOH$; Calc'd: C, 63.71; H, 6.85; N, 9.16. Found: C, 63.40; H, 6.70; N, 8.97.

EXAMPLE 2

(3,4-Dihydro-benzo[1,4]oxazine-3-ylmethyl)-[cis-4-(5-fluoro-1H-indol-3-yl)-cyclohexyl]-amine) and (3,4-Dihydro-benzo[1,4]oxazine-3-ylmethyl)-[trans-4-(5-fluoro-1H-indol-3-yl)-cyclohexyl]-amine A solution of 4-(5-fluoro-1H-indol-3-yl)-cyclohexanone (0.578 g, 2.5 mmol), 3-aminomethyl-1,4-benzoxazine (0.411 g, 2.5 mmol), sodium triacetoxyborohydride (0.78 g, 3.5 mmol) and acetic acid (0.14 ml, 2.5 mmol) in 1,2-dichloroethane (11 ml) was allowed to stir at room temperature for 5 hours. The reaction was quenched with 1N sodium hydroxide, extracted with methylene chloride. The combined organic extracts were washed with brine, dried over anhydrous sodium sulfate, filtered and concentrated. The product was purified by chromatography (EtOAc/MeOH/NH$_4$OH: 99/1/0.5) to afford 0.63 g (66%) of the cis isomer as an oil. The fumarate salt of the cis isomer was prepared in isopropanol: mp 208–209° C.

Elemental analysis for $C_{23}H_{26}FN_3O•0.5C_4H_4O_4•0.3H_2O•0.24i-PrOH$; Calc'd: C, 67.55; H, 6.73; N, 9.19. Found: C, 67.75; H, 6.69; N, 8.99.

The trans isomer was isolated in 33% yield (0.32 g) as an oil. The fumarate salt of the trans isomer was prepared in isopropanol: mp 275–277° C. (dec).

Elemental analysis for $C_{23}H_{26}FN_3O \cdot 0.5C_4H_4O_4 \cdot 0.3H_2O$; Calc'd: C, 67.79; H, 6.51; N, 9.49. Found: C, 67.58; H, 6.47; N, 9.18.

The activity of the present compounds is demonstrated by the following standard pharmacological test procedures.

The PCR cloning of the human 5-$HT_{1A}$ receptor subtype from a human genomic library has been described previously Chanda et al., *Mol. Pharmacol.*, 43:516 (1993). A stable Chinese hamster ovary cell line expressing the human 5-$HT_{1A}$ receptor subtype (5-$HT_{1A}$.CHO cells) was employed throughout this study. Cells were maintained in DMEM supplemented with 10% foetal calf serum, non-essential amino acids and penicillin/streptomycin.

Cells were grown to 95–100% confluency as a monolayer before membranes were harvested for binding studies. Cells were gently scraped from the culture plates, transferred to centrifuge tubes, and washed twice by centrifugation (2000 rpm for 10 min., 4° C.) in buffer (50 mM Tris; pH 7.5). The resulting pellets were aliquoted and placed at −80° C. On the day of assay, the cells were thawed on ice, and resuspended in buffer. Studies were conducted using [$^3$H]8-OH-DPAT as the radioligand. The binding assay was performed in 96 well microtiter plates in a final total volume of 250 $\mu$L of buffer. Competition experiments were performed by using 7 concentrations of unlabelled drug and a final ligand concentration of 1.5 nM. Non-specific binding was determined in the presence of 10 $\mu$M 5HT. Saturation analysis was conducted by using [$^3$H]8-OH-DPAT at concentrations ranging from 0.3–30 nM. Following a 30 minute incubation at room temperature, the reaction was terminated by the addition of ice cold buffer and rapid filtration using a M-96 Brandel Cell Harvester (Gaithersburg, Md) through a GF/B filter presoaked for 30 minutes in 0.5% polyethyleneimine.

A protocol similar to that used by Cheetham et al., *Neuropharmacol.*, 32:737 (1993) was used to determine the affinity of compounds for the serotonin transporter. Briefly, frontal cortical membranes prepared from male Sprague-Dawley rats were incubated with $^3$H-paroxetine (0.1 nM) for 60 min at 25° C. All tubes also contained either vehicle, test compound (one to eight concentrations), or a saturating concentration of fluoxetine (10 $\mu$M) to define specific binding. All reactions are terminated by the addition of ice cold Tris buffer followed by rapid filtration using a Tom Tech filtration device to separate bound from free $^3$H-paroxetine. Bound radioactivity was quantitated using a Wallac 1205 Beta Plate® counter. Nonlinear regression analysis was used to determine $IC_{50}$ values which were converted to Ki values using the method of Cheng and Prusoff, *Biochem. Pharmacol.*, 22:3099 (1973); Ki=IC50/((Radioligand conc.)/(1+KD)).

The [$^{35}$S]-GTPγS binding assay was similar to that used by Lazareno and Birdsall, *Br. J. Pharmacol.* 109:1120 (1993). Briefly, 5-$HT_{1A}$ cloned receptor membrane fragments (as used for 5-$HT_{1A}$ receptor binding assays) were stored at −70° C. until needed. When needed, membranes were rapidly thawed, centrifuged at 40,000 ×g for 10 minutes and resuspended at 4° C. for 10 minutes in assay buffer (25 mM HEPES, 3 mM $MgCl_2$, 100 mM NaCl, 1 mM EDTA, 10 uM GDP, 500 mM DTT, pH 8.0). These membranes were then incubated for 30 min at 30° C. with [$^{35}$S]GTPgS (1 nM) in the presence of vehicle, test compound (one to eight concentrations), or excess 8-OH-DPAT to define maximum agonist response. All reactions are terminated by the addition of ice cold Tris buffer followed by rapid filtration using a Tom Tech® filtration device to separate bound from free [$^{35}$S]GTPgS. Agonists produce an increase in the amount of [$^{35}$S]GTPgS bound whereas antagonists produce no increase in binding. Bound radioactivity was counted and analyzed as above.

The following assays were performed by incubating the cells with DMEM containing 25 mM HEPES, 5 mM theophylline and 10 $\mu$M pargyline for a period of 20 minutes at 37° C. Functional activity was assessed by treating the cells with forskolin (1 uM final concentration) followed immediately by test compound (6 concentrations) for an additional 10 min at 37° C. In separate experiments, 6 concentrations of antagonist were preincubated for 20 min prior to the addition of 10 nM 8-OH-DPAT and forskolin. The reaction was terminated by removal of the media and addition of 0.5 ml ice cold assay buffer. Plates were stored at −20° C. prior to assessment of cAMP formation by a cAMP SPA assay (Amersham).

The results of the tests with the compounds of Examples 1 and 2 are given in the following table.

| Example | Ki (nM) ST [$^3$H]paroxetine | Ki (nM) 5HT1A [$^3$H]DPAT |
| --- | --- | --- |
| 1 (cis) | 44 | 2432 |
| 1 (trans) | 24 | 44% @ 1 $\mu$M |
| 2 (cis) | 34% @ 1 $\mu$M | 9% @ 1 $\mu$M |
| 2 (trans) | 10 | 20% @ 1 $\mu$M |

The compounds of this invention may be administered orally or parenterally, neat or in combination with conventional pharmaceutical carriers. Applicable solid carriers can include one or more substances which may also act as flavoring agents, lubricants, solubilizers, suspending agents, fillers, glidants, compression aids, binders or tablet-disintegrating agents or an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Any of the solid carriers known to those skilled in the art may be used with the compounds of this invention. Particularly suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidone, low melting waxes and ion exchange resins.

Liquid carriers may be used in preparing solutions, suspensions, emulsions, syrups and elixirs of the compounds of this invention. The compounds of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above, e.g., cellulose derivatives, preferably sodium carboxymethyl cellulose solution), alcohols (including monohydric alcohols and polyhydric alcohols, e.g., glycols) and their derivatives and oils (e.g., fractionated coconut oil and arachis oil). For parenteral administration, the carrier can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilized by, for example, intramuscular, intraperitoneal or subcutaneous injection. Sterile solutions can also be administered intravenously. Compositions for oral administration may be either liquid or solid composition form.

Preferably, the pharmaceutical compositions containing the compounds of this invention are in unit dosage form, e.g., tablets or capsules. In such form, the compositions may be sub-divided in unit doses containing appropriate quantities of the present compounds. The unit dosage forms can be packaged compositions, for example, packeted powders, vials, ampoules, prefilled syringes or sachets containing liquids. Alternatively, the unit dosage form can be, for example, a capsule or tablet itself, or it can be the appropriate number of any such compositions in package form.

The therapeutically effective amount of the compounds of this invention that is administered and the dosage regimen depends on a variety of factors, including the weight, age, sex, and medical condition of the subject, the severity of the disease, the route and frequency of administration, and the specific compound employed, and thus may vary widely. However, it is believed that the pharmaceutical compositions may contain the compounds of this invention in the range of about 0.1 to about 2000 mg, preferably in the range of about 0.5 to about 500 mg and more preferably between about 1 and about 100 mg. Projected daily dosages of active compound are about 0.01 to about 100 mg/kg body weight. The daily dose can be conveniently administered two to four times per day.

The present invention may be embodied in other specific forms without departing from the spirit and essential attributes thereof and accordingly, reference should be made to the appended claims, rather than to the foregoing specification, as indicating the scope of the invention.

What is claimed is:

1. A compound of the formula

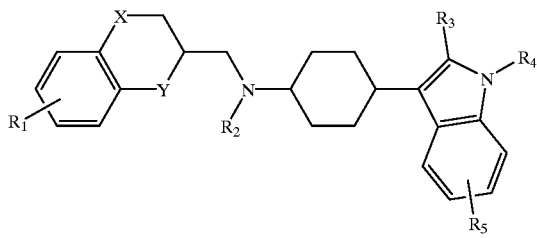

wherein:

$R_1$ and $R_5$ are each, independently, hydrogen, halogen, lower alkoxy, lower alkyl, cyano, or trifluoromethyl;

$R_2$ and $R_4$ are each, independently, hydrogen, lower alkyl, phenyl, or substituted phenyl;

$R_3$ is hydrogen or lower alkyl; and

X and Y are each, independently, O, $NR_6$, or $CH_2$, wherein
$R_6$ is hydrogen, lower alkyl, phenyl, or substituted phenyl; or pharmaceutically acceptable salts thereof.

2. A compound according to claim 1 wherein:

$R_1$ and $R_5$ are each, independently, hydrogen, or halogen;

$R_2$ and $R_4$ are each hydrogen;

$R_3$ is hydrogen; and

X and Y are each, independently, O or $NR_6$, wherein $R_6$ is hydrogen; or pharmaceutically acceptable salts thereof.

3. The compound according to claim 1, which is (3,4-Dihydro-benzo[1,4]oxazine-2-ylmethyl)-[cis-4-(5-fluoro-1H-indol-3-yl)-cyclohexyl]-amnine.

4. The compound according to claim 1, which is (3,4-Dihydro-benzo[1,4]oxazine-2-ylmethyl)-[trans-4-(5-fluoro-1H-indol-3-yl)-cyclohexyl]-amine.

5. The compound according to claim 1, which is (3,4-Dihydro-benzo[1,4]oxazine-3-ylmethyl)-[cis-4-(5-fluoro-1H-indol-3-yl)cyclohexyl]-amine.

6. The compound according to claim 1, which is (3,4-Dihydro-benzo[1,4]oxazine-3-ylmethyl)-[trans-4-(5-fluoro-1H-indol-3-yl)-cyclohexyl]-amine.

7. A pharmaceutical composition comprising a compound of the formula

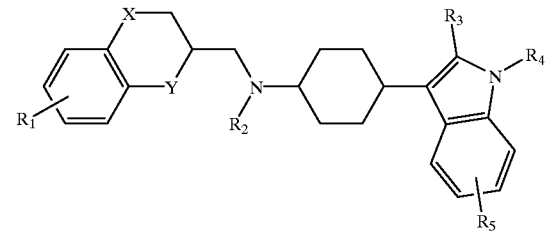

wherein:

$R_1$ and $R_5$ are each, independently, hydrogen, halogen, lower alkoxy, lower alkyl, cyano, or trifluoromethyl;

$R_2$ and $R_4$ are each, independently, hydrogen, lower alkyl, phenyl, or substituted phenyl;

$R_3$ is hydrogen or lower alkyl; and

X and Y are each, independently, O, $NR_6$, or $CH_2$, wherein
$R_6$ is hydrogen, lower alkyl, phenyl, or substituted phenyl; or pharmaceutically acceptable salts thereof.

8. A method for alleviating the symptoms of depression in a patient in need thereof, comprising administering to said patient an antidepressant effective amount of a compound of the formula

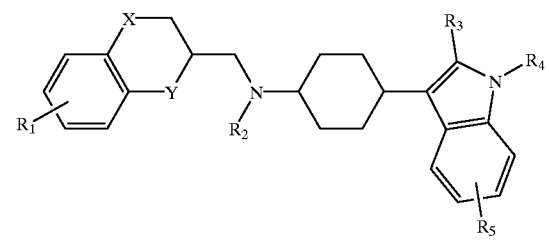

wherein:

$R_1$ and $R_5$ are each, independently, hydrogen, halogen, lower alkoxy, lower alkyl, cyano, or trifluoromethyl;

$R_2$ and $R_4$ are each, independently, hydrogen, lower alkyl, phenyl, or substituted phenyl;

$R_3$ is hydrogen or lower alkyl; and

X and Y are each, independently, O, $NR_6$, or $CH_2$, wherein
$R_6$ is hydrogen, lower alkyl, phenyl, or substituted phenyl; or pharmaceutically acceptable salts thereof.

* * * * *